US009655430B2

(12) United States Patent
Park

(10) Patent No.: US 9,655,430 B2
(45) Date of Patent: May 23, 2017

(54) DOUBLE COLORED NAIL APPLIQUE HAVING AN ULTRAVIOLET CURED LAYER, METHOD OF MAKING AND USING

(71) Applicant: Fa Young Park, Clifton, NJ (US)

(72) Inventor: Fa Young Park, Clifton, NJ (US)

(73) Assignee: Park Global Holdings, LLC, Clifton, NJ (US)

( * ) Notice: Subject to any disclaimer, the term of this patent is extended or adjusted under 35 U.S.C. 154(b) by 0 days.

(21) Appl. No.: 14/337,698

(22) Filed: Jul. 22, 2014

(65) Prior Publication Data

US 2014/0326266 A1 Nov. 6, 2014

Related U.S. Application Data

(63) Continuation-in-part of application No. 13/859,563, filed on Apr. 9, 2013, and a continuation-in-part of application No. 11/126,862, filed on May 11, 2005, now abandoned, application No. 14/337,698, which is a continuation-in-part of application No. 11/126,862.

(60) Provisional application No. 61/621,887, filed on Apr. 9, 2012, provisional application No. 61/799,386, filed on Mar. 15, 2013.

(51) Int. Cl.
*A61K 31/33* (2006.01)
*A45D 29/00* (2006.01)
*B05D 3/06* (2006.01)

(52) U.S. Cl.
CPC ........... *A45D 29/001* (2013.01); *B05D 3/067* (2013.01)

(58) Field of Classification Search
None
See application file for complete search history.

(56) References Cited

U.S. PATENT DOCUMENTS 4,903,840 A * 2/1990 So ........................ A45D 29/001 132/73
6,296,836 B1 * 10/2001 Engler ................. A45D 29/004 132/73
8,176,924 B2 * 5/2012 Schneider ............. A45D 31/00 132/73

FOREIGN PATENT DOCUMENTS

WO WO 2005/070048 * 8/2005

* cited by examiner

*Primary Examiner* — Craig Ricci
(74) *Attorney, Agent, or Firm* — Carrie Marlene Stroup

(57) ABSTRACT

A double colored nail appliqué, method of manufacturing and using, the appliqué having two different decorations sequentially via the user removing the top coat of a second colored enamel layer to expose an underlying base coat with a different, first colored enamel layer. The base coat is covered by a UV adhesive layer that protects it during the removal of the top coat. The nail appliqué may further comprise a metallic foil layer directly above or below the UV layer; a design imprinted on the top or bottom coat of enamel; and, a clear coat of enamel covering the top coat. Removal of the top coat(s) by the user does not damage the underlying coats/layers. Therefore, one nail appliqué can be used to offer two different appearing manicures without having to apply a new nail appliqué.

8 Claims, 5 Drawing Sheets

DOUBLE COLORED NAIL APPLIQUE HAVING AN ULTRAVIOLET CURED LAYER, METHOD OF MAKING AND USING

CROSS-REFERENCE TO RELATED APPLICATIONS

The present application is a continuation-in-part of U.S. Ser. No. 13/859,563 filed on Apr. 9, 2013 and is a continuation-in-part of U.S. Ser. No. 11/126,862, filed May 11, 2005, U.S. Ser. No. 13/859,563 claims the benefit of U.S. Provisional Patent Application No. 61/621,887, filed Apr. 9, 2012, and U.S. Provisional Patent Application No. 61/799,386, filed Mar. 15, 2013. All of the aforesaid applications are incorporated by reference herein in their entireties.

FIELD OF THE INVENTION

The present invention relates to the field of nail polish and nail decorations, and, more specifically, to nail appliqués for adorning a fingernail or toenail.

BACKGROUND OF THE INVENTION

The use of an instant fingernail coating product whereby nail polish is applied to a fingernail by adhesively securing to it in a dry or in a semi-dried form of nail polish has become a popular method of providing a manicure. Such products, also known as “nail appliqués”, allow a user to rapidly decorate finger or toe nails with colors, designs or images, or with metallic sheens. For example, U.S. application Ser. No. 11/126,862, filed May 11, 2005 discloses the product and method of manufacturing semi-dry nail appliqués. Because of its semi-dried state, a nail appliqué easily stretches, conforms and adheres to a nail after which it completely cures and dries.

Additionally, the use of ultraviolet (UV) radiation on a nail decoration is known in the art as a form of curing nail gels. For example, the U.S. Publication 2012/0103354 (i.e. U.S. patent application Ser. No. 13/859,563 filed on Apr. 9, 2013) discusses many desirable features of the UV gel: beautiful, smooth, glassy, and durable finish. However, due to its cross-linking properties, once applied on a nail, the removal of a UV gel is time-consuming and difficult. A conventional technique to remove a UV gel involves the following steps: buffing the surface of the nails, soaking the nails in harsh solvents such as a high concentration of acetone for a period of time, or alternatively wrapping aluminum foils around the nails with acetone soaked cotton balls, and then scrapping off the UV gel.

Due to a cured UV gels hard and ridged physical properties, the use of UV gel in a semi-dry nail appliqué is known to be very difficult in practice. This is because the UV gel rigid cured state does not fit well with the appliqués which require conformity to nails, flexibility and stretch-ability.

These previous dry (e.g. artificial nails) or semi-dry nail coating products are not well adapted to providing two or more different looks, decorations or shades sequentially over time. For example, a user may wish to decorate a nail with a particular design or shade and later decorate the nail with a different color, design or any combination thereof, without having to completely replace the nail appliqué. This is especially the case when the appliqué comprises a UV layer that is difficult to remove, and requires exposing the nail to harsh chemicals.

It would be desirable to fashion a nail appliqué that provides a novel way the users may easily decorate their nails with two or more different decoration comprising colors, designs, images and/or patterns. This problem is solved by the current invention, which is directed to a nail appliqué comprising at least one layer of a novel, flexible UV radiation-curable gel that protects an underlying layer of a first enamel color/design when the user removes an upper layer of a second enamel color/design.

SUMMARY OF THE INVENTION

The current invention is directed to a novel product, and its method of manufacturing and method of use of an appliqué providing at least two nail decorations sequentially—one each of a first and second layer of partially cured nail enamel, wherein a UV gel layer provides a buffer between the two decorative layers in an appliqué. A layer of metallic foil material may also lie directly above or below the UV layer to enhance the decoration of the enamel layers.

A nail appliqué according to an embodiment of the present invention includes a self-adhesive nail appliqué having from bottom to top: a removable substrate; a first adhesive layer; a first partially-cured enamel base coat on the first adhesive layer; a UV layer on the base coat; and a second partially-cured enamel top coat on the UV layer, wherein the first and second coats or layers comprise different decorations, attributable, for example, to different colors and/or designs. An aesthetic design made from enamel and/or pigmented UV cured polymer, may be applied to the first and/or second coat/layers. The nail appliqué may further comprise a metallic foil layer to enhance the decoration of the enamel layers.

In some other embodiments, the nail appliqué is stretchable and all the layers are stretchable at substantially the same rates as each other. In yet other embodiments, all the layers are coextensive with each other in an uncured state, a partially-cured state, and a cured state. In further embodiments, a metallic foil layer is directly on top of, beneath, or embedded within the UV layer and is a single layer coextensive with the second adhesive UV layer.

The method of manufacturing the self-adhesive nail appliqué according to an embodiment of the present invention includes the steps of forming a first adhesive layer; forming a first colored enamel layer on the adhesive layer; forming a UV layer on the first enamel layer; and forming a second colored enamel layer on the UV layer. In some embodiments, the method may further comprise forming a metallic foil layer on the UV layer or beneath the UV layer and on the first colored enamel layer. In some embodiments, the step of forming the UV layer includes the step of exposing the adhesive to ultraviolet radiation. In some embodiments, the method may further comprise adding a design onto either the first or the second colored layer of enamel, or both. In some embodiments, a top coat may be provided on the second enamel layer.

The method of use comprises providing a nail appliqué with a first decoration from one of the various embodiments disclosed herein, detaching the first adhesive layer from a substrate layer; applying the first adhesive layer onto a surface of a human nail wherein the adhesive layer secures the nail appliqué to the surface of the nail; filing or cutting the nail appliqué to more closely conform to the shape of the human nail, and allowing the nail appliqué to dry completely; and, then removing by the user at a later time, the top coats of enamel down to the UV layer without damaging the nail appliqué to provide the appliqué with a second decoration.

In the various embodiments, the UV layer is formulated and cured to stay intact and protects the first enamel layer when the third layer (e.g. metallic foil and/or second enamel layer) is removed via standard means—e.g. nail polish remover or rubbing with a soft cloth.

In some embodiments, the UV layer may be clear translucent, translucently pigmented, or non-translucent. In some other embodiments, one or more layers may be pigmented translucent, such as the combination of layers provides endless color combinations. For instance, the first layer may be translucently pigmented with red, and the second layer translucently pigmented with blue, which in combination provides purple color; when the second layer is removed, the user enjoys red color. In some other embodiments, an image or design atop may be provided on either the first or the second layer, or both, of the two enamel layers. In some other embodiments, a metallic foil layer may be provided on the UV layer. Nail appliqués comprising a metallic foil layer is disclosed in U.S. Publication 2013/0220355. In some other embodiments, the nail appliqué is stretchable. In yet other embodiments, all the layers are coextensive with each other in an uncured state, a partially-cured state, and a cured state. In some embodiments, a top coat may be provided on the second enamel layer.

A primary advantage of the various embodiments disclosed herein is a single nail applique comprising two or more decorations, wherein the user merely removes the second layer of nail enamel comprising a second design/color to expose the underlying first layer with a different first design/color that is protected by the UV cured layer atop it. When the user removes the second layer of nail enamel, they do not risk damaging the underlying first layer of nail enamel because it is protected by the UV cured layer and/or metallic foil layer. Therefore, the user can easily change the decoration of their manicure merely by removing the second top layer of nail enamel (e.g. changing it by removing a red second top layer to expose a blue first layer with a translucent UV coating).

Another advantage of the various embodiments is that the life of the manicure is substantially prolonged (e.g. doubled) because the user has two color/design enamel layers within one nail appliqué. For example, when the second enamel layer beings to wear off, the user can remove it to expose the first enamel layer with the UV cured layer with or without the metallic foil layer atop it, instead of having to apply a completely new nail appliqué.

The various embodiments of the nail appliqué provide an unlimited combination of decorations as a result of: the first and second enamel layers made of different translucent pigments and/or solid color and/or they may have an aesthetic design printed on them; the UV layer may be may be clear translucent, translucently pigmented, or non-translucent; there may or may not be a metallic foil layer residing directly above or below the UV layer; and, there may or may not be a top clear coat above the second color/design layer.

For example, a nail appliqué with a translucently pigmented red second layer, a UV layer beneath it, and a translucently pigments blue first layer will have the decoration of purple. But, when the second layer is removed with nail polish, then the nail appliqué has a high gloss blue decoration.

BRIEF DESCRIPTION OF THE DRAWINGS

For a more complete understanding of the present invention, reference is made to the following detailed description of the invention considered in conjunction with the accompanying drawings, in which.

DETAILED DESCRIPTION OF THE INVENTION

Nail Appliqués Double Colored/Design

In some embodiments, the present invention includes a multi-layered nail appliqué having a different color/design in first and second layer of nail enamel. In a method according to an embodiment of the present invention, the nail appliqué is built up in a layer-by-layer fashion on top of a releasable substrate. The nail appliqué is soft and stretchable to cover a user's fingernail or toenail, but is hardened (e.g., with the aid of a user's body heat, or at room temperature) when it is applied to the fingernail or toe nail. For the purposes of the present disclosure, fingernails and toenails are referred to, collectively, as "nails".

Figure 1:
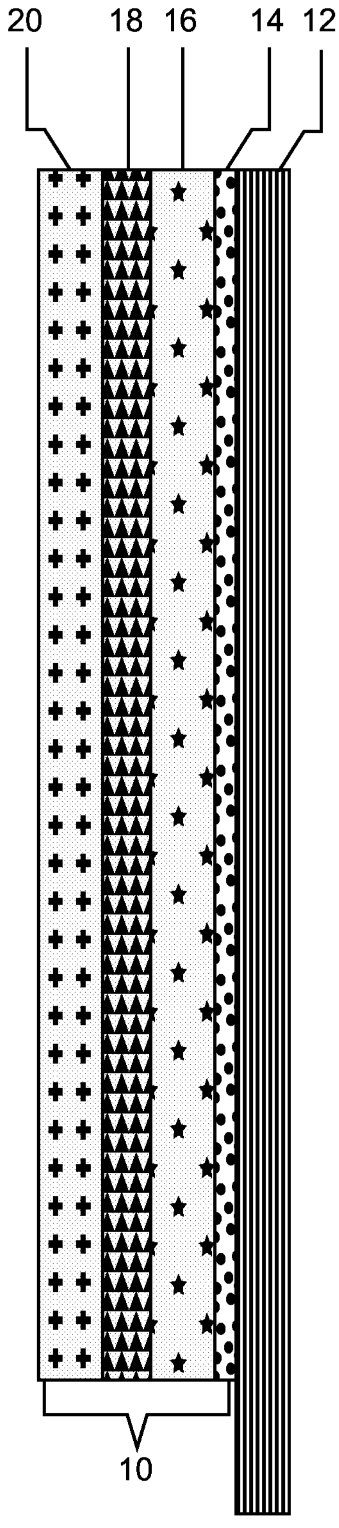
FIG. 1 is a schematic diagram of a vertical cross-section of a double color/design nail appliqué on a removable substrate according to a first embodiment of the present invention.

FIG. 1 is a schematic diagram of a vertical cross-section of nail appliqué 10 according to an embodiment of the present invention. In one embodiment, the nail appliqué 10 is provided adhered to a removable substrate 12 from which the nail appliqué 10 can be detached. Turning to FIG. 1, a nail appliqué 10 according to an embodiment of the present invention is a multi-layer structure including: a first adhesive layer 14, comprising an adhesive suitable for adhering the nail appliqué to the nail and removably adhering the nail appliqué to the substrate 12; a first, base coat 16 comprising partially dried-cured nail enamel residing on the first adhesive layer 14; a second adhesive UV cured layer 18 residing on the base coat 16; and, a second coat 20 comprising a partially dried-cured nail enamel residing on the second adhesive UV cured layer 18. The second coat 20 is a different color, with or without an imprinted design, than the base coat 16. An aesthetic design may be printed on the first and/or second coat to give a different decoration to each. For example, the base coat 16 and the second coat 20 may comprise the same color of enamel but have a different design printed thereon, thus giving a different decoration to the appliqué when the second coat 20 with a second design imprinted thereon is manually removed by the user to expose the base coat 16 with a first imprinted design.

The nail applique may further comprise a top coat of a clear nail enamel (not shown) covering the second coat 20.

The second adhesive layer 18 includes an adhesive substance that may be cured (e.g., gelled and/or hardened) by exposure to ultraviolet radiation (also referred to as "UV radiation"), and is also referred to herein as a "UV adhesive layer".

Nail Appliqués with Metallic Foil

Figure 2:
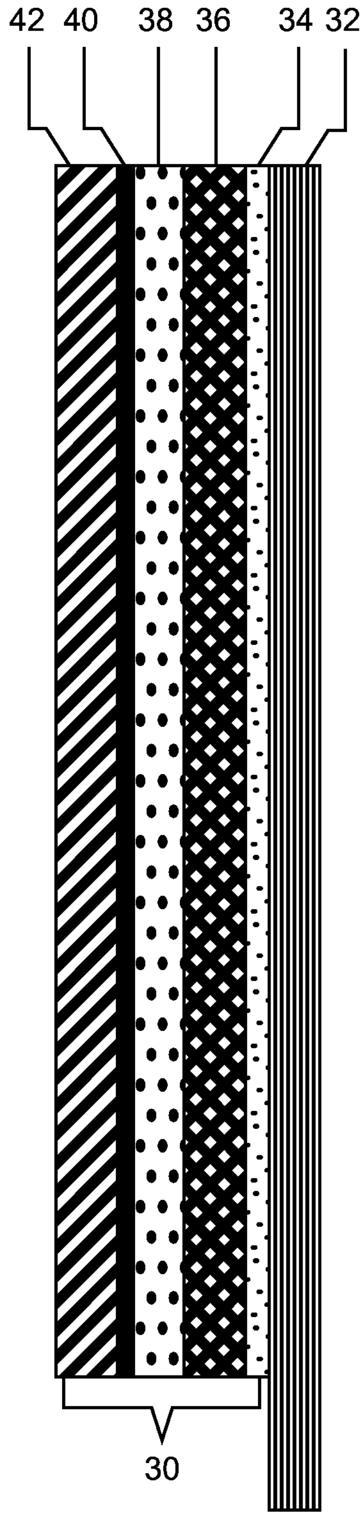
FIG. 2 is a schematic diagram of a vertical cross-section of a multilayer foil nail appliqué on a removable substrate according to a second embodiment of the present invention wherein the a UV layer resides directly beneath a metallic foil layer.

In some embodiments, the present invention includes a dual color/design multi-layered nail appliqué having metallic foil or film as at least one of the layers ("nail appliqué) residing between the two layers of partial dried nail enamel of different color/designs and a UV cured layer. In a method according to an embodiment of the present invention, the nail appliqué is built up in a layer-by-layer fashion on top of a releasable substrate. By way of a non-limiting example as illustrated in FIG. 2, the layers may comprise from bottom to top: adhesive material; a first nail enamel layer with a first design/color; a UV cured layer; a metallic foil layer (optional); a second nail enamel layer with a second design/color; and, a top coat of clear enamel (optional). The nail appliqué is soft and stretchable to cover a user's fingernail or toenail, but is hardened (e.g., with the aid of a user's body heat, or at room temperature) when it is applied to the fingernail or toe nail.

FIG. 2 is a schematic diagram of a vertical cross-section of nail appliqué 30 according to an embodiment of the present invention comprising two layers of partially dried enamel of different colors and/or designs. (It is noted that "designs" are optional throughout the embodiments disclosed herein and are not specifically depicted in FIGS. 1-4 because they do not comprise a complete layer within the appliqué, but are rather printed onto the base or top enamel layer by methods well known in the art). In one embodiment, the nail appliqué 30 is provided adhered to a removable substrate 32 from which the nail appliqué 30 can be detached.

As illustrated in FIG. 2, a nail appliqué 30 according to an embodiment of the present invention is a multi-layer structure including: a first adhesive layer 34, comprising an adhesive suitable for adhering the nail appliqué to the nail and removably adhering the nail appliqué to the substrate 32; a base coat 36 comprising a partially dried-cured nail enamel of color/design (1) residing on the first adhesive layer 34; a second UV adhesive layer 38 residing on the base coat 36; a layer of metallic foil or film 40 residing on the second UV adhesive layer 38; and a top coat 42 of partially dried-cured nail enamel of color/design (2) covering the metallic foil or film. The difference in the decoration of the base coat 36 and the top coat 42 is attributable to their different color and/or design, as well as the layer of UV gel and metallic foil covering the base coat 36.

The second UV adhesive layer 38 includes an adhesive substance that may be cured (e.g., gelled and/or hardened) by exposure to ultraviolet radiation (also referred to as "UV radiation"), and is also referred to herein as a "UV adhesive layer".

Figure 3:
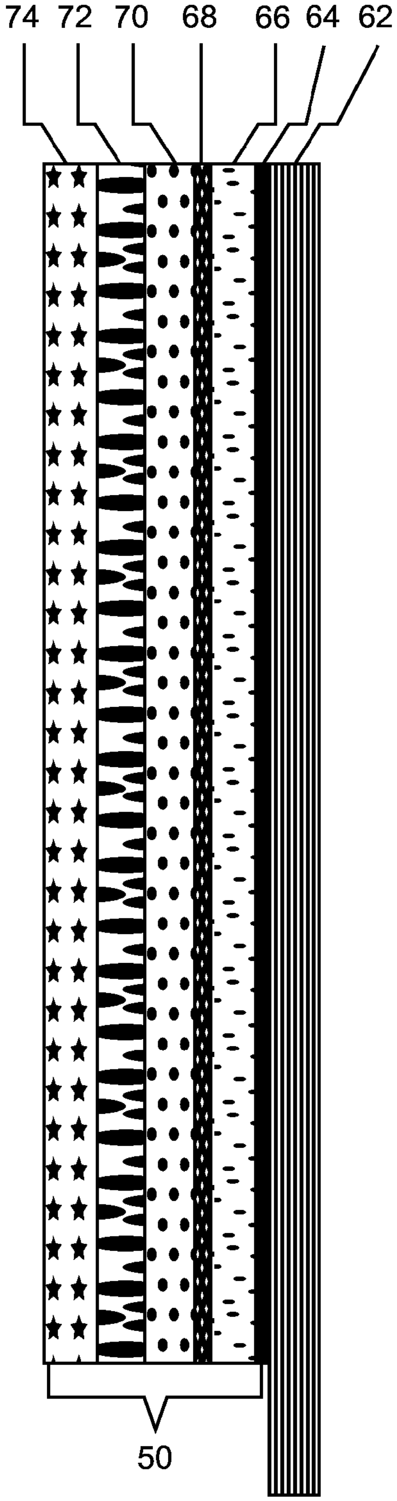
FIG. 3 is a schematic diagram of a vertical cross-section of a multilayer foil nail appliqué on a removable substrate according to a third embodiment of the present invention wherein the metallic foil layer resides directly beneath the UV layer, and the top coat is clear enamel.

FIG. 3 is a schematic diagram of a vertical cross-section of a nail appliqué 50 according to an embodiment of the present invention. In one embodiment, the nail appliqué 50 is provided adhered to a removable substrate 62 from which the nail appliqué 50 can be detached. As illustrated in FIG. 3, a nail appliqué 50 according to an embodiment of the present invention is a multi-layer structure including: a first adhesive layer 64, comprising an adhesive suitable for adhering the nail appliqué to the nail and removably adhering the nail appliqué to the substrate 62; a base coat 66 comprising partially dried nail enamel residing on the first adhesive layer 64; a layer of metallic foil or film 68 residing on the base coat 66; a UV adhesive layer 70 residing on the metallic foil or film 68; a second coat 72 comprising partially dried nail enamel layer with a second design/color residing on the UV adhesive layer 70; and, a top coat of a clear nail enamel 74 covering the second coat 72. The UV adhesive layer 70 includes an adhesive substance that may be cured (e.g., gelled and/or hardened) by exposure to ultraviolet radiation (also referred to as "UV radiation").

Figure 4:
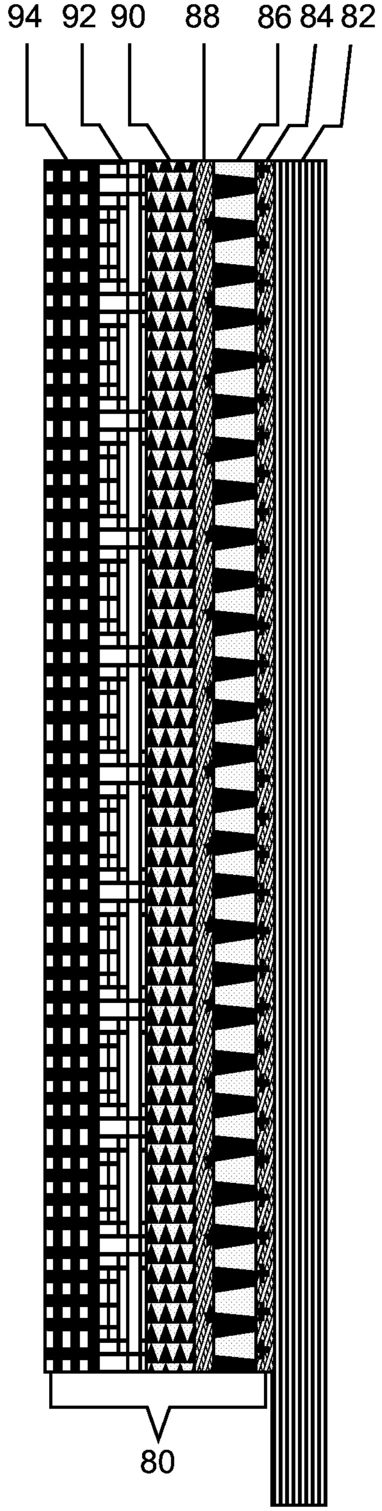
FIG. 4 is a schematic diagram of a vertical cross-section of a multilayer foil nail appliqué on a removable substrate according to a fourth embodiment of the present invention the metallic foil layer resides directly beneath the UV layer, and the top coat is a design printed on the second enamel layer; and, FIG. 5 is a schematic top plan view of a set of nail appliqués after they have been cut from a laminated sheet prepared according to an embodiment of a method of the present invention.

FIG. 4 is a schematic diagram of a vertical cross-section of nail appliqué 80 according to an embodiment of the present invention. In one embodiment, the nail appliqué 80 is provided adhered to a removable substrate 82 from which the nail appliqué 80 can be detached. As illustrated in FIG. 4, a nail appliqué 80 according to an embodiment of the present invention is a multi-layer structure including: a first adhesive layer 84, comprising an adhesive suitable for adhering the nail appliqué to the nail and removably adhering the nail appliqué to the substrate 82; a base coat 86 comprising partially dried/cured nail enamel residing on the first adhesive layer 84; a layer of metallic foil or film 88 residing on the base coat 86; a UV adhesive layer 90 residing on the metallic foil or film 88; a second coat 92 comprising partially dried nail enamel layer with a second design/color residing on the UV adhesive layer 90; and, a design pattern 94 imprinted in the second coat 92. The UV adhesive layer 90 includes an adhesive substance that may be cured (e.g., gelled and/or hardened) by exposure to ultraviolet radiation (also referred to as "UV radiation").

Turning now to the materials that may be used to form the layers of the nail appliqué 10, 30, 50, 80 of FIGS. 1-4, in it may first be noted that suitable materials for each of the adhesive or nail enamel layers may be obtained commercially, or may be developed on a custom basis using materials and methods known in the art. In embodiments of the invention, the aforesaid layers should maintain their dimensional stability during curing in the manufacturing process and/or while on the user's nails. If the dimensions of the layers do change, such changes should occur to a similar degree across each of the layers such that the layers remain co-extensive (i.e., cover each other to the same extent) to avoid wrinkling or distortion of the nail appliqué, or, more specifically, the foil layer. The dimensional stability of the metallic foil or film layer 40, 68, 88 in FIGS. 2-4 will typically be less of a concern for reasons discussed elsewhere herein. The materials used for the various layers should also, when working together, provide a structure having physically properties (e.g., stretch ability, flexibility, tear resistance, etc.) that are desired in the final product (i.e., the nail appliqué), and should stretch or flex without wrinkling the appliqué or the foil layer. These properties may be similar to those of certain nail enamel appliqués presently known in the art, such as those described in U.S. patent application Ser. No. 11/126,862, filed May 11, 2005, (published as U.S. Patent Publication No. 2005/0255061, published Nov. 17, 2005), the entire disclosures of both of which are incorporated by reference herein.

Turning to the first adhesive layer 14, 34, 64, 84 in FIGS. 1-4, respectively, the adhesive used therein should be able to adhere firmly to a nail when cured. The adhesive may be applied to the substrate 12, 32, 62, 82 in FIGS. 1-4, respectively, as a liquid or melted from a hardened state, and may contain solvents that volatilize readily at a human body temperature or below, such as low-molecular-weight acetates or alcohols. The adhesive of the first adhesive layer 14, 34, 64, 84 should also be of a type that will release readily from the substrate 12, 32, 62, 82, which may be made of a material, such as a thin sheet of silicon-coated release liner paper or aluminum laminate plastic film. A suitable thickness for the first adhesive layer in some embodiments of the present invention would be about 10-15% of the total thickness dof the finished appliqué. Adhesives and substrates suitable for use in the present invention are similar to those discussed further in the aforesaid U.S. patent application Ser. No. 11/126,862 with regard to nail enamel appliqués. Exemplary adhesives suitable for the present invention include acrylic co-polymer adhesives.

Nail appliqué with partially-dried/cured enamel: Turning to the base coat of the first nail enamel layer with a first design/color 16, 36, 66, 86, and the second nail enamel layer with a second design/color 20, 42, 72, 92 in FIGS. 1-4, respectively, it should be noted that in various embodiments of the present disclosure, these coats may be formed from commercially available or custom-made nail enamels. Preferably, the enamel layers are comprised of liquid nail enamel that is applied to a substrate. Before the enamel is fully dried—it is sealed in a protective package to prevent complete drying. The enamel thus fully cures on a fingernail once applied thereto—similar to the manner in which conventional nail polish cures.

The nail enamel may be organic solvent-based, or aqueous-based, or be of a UV-curable type. Desirable physical properties and compositions of the nail enamels will depend on such factors as the method of applying the two color/design layers, or the temperature at which the layers are to be cured. Organic solvent-based nail enamels having viscosities of 1500-4000 centipoise (60 rpm) at room temperature (e.g., about 20° C.) may have particular utility in the present invention. Nail enamel properties and formulations are discussed in the aforesaid U.S. patent application Ser. No. 11/126,862 with regard to nail enamel appliqués, any may readily be adapted by those having ordinary skill in the art to produce clear coats suitable for use with the present invention.

Design Layers:

the base coat of the first nail enamel layer with a first design/color 16, 36, 66, 86, and the second nail enamel layer with a second design/color 20, 42, 74, 94 in FIGS. 1-4, respectively, may further comprise a pattern creating an artistic or ornamental "design" imprinted on colored or clear enamel. The design pattern does not normally comprise a complete layer (e.g. is not co-extensive). Methods of imprinting the designs onto nail appliqués are well known in the art. Exemplary methods are disclosed in US 20050255061 filed May 11, 2005.

A variety of combinations of the two layers are envisioned herein, such as: a base coat of a solid first color and a second top coat of a solid second color comprising a design imprinted thereon that when manually removed by the user (e.g. nail polish or rubbing with soft cloth) leaves the base coat displaying the first solid color and protected by a UV cured layer with or without a metallic foil layer adjacent to the UV layer; vice versa—a base coat with a solid first color comprising a design pattern imprinted thereon and protected by a UV cured layer with or without a metallic foil layer; two solid colored layers; a base coat with a design imprinted thereon that is covered by a protective UV layer that is exposed when a second colored layer is removed.

In one embodiment of the present invention, the top coat 74 in FIG. 3, is made from a clear (e.g., transparent or translucent) enamel, so that the underlying layer may be seen. It may also function to protect the appliqué from chipping and other damage. In some embodiments, the clear coat may include a color, or may include additives (e.g., glitter or mica chips) to enhance the decoration of the finished appliqué.

The layer directly beneath the UV layer (e.g. the base coat in FIGS. 1, 2, or the metallic foil in FIGS. 3, 4) functions as a mechanical barrier between the first adhesive layer and the UV adhesive layer, and also provide a smooth surface for application of the UV adhesive layer.

The UV adhesive layer 18, 38, 56, 76 in FIGS. 1-4, respectively, may include any of a broad range of materials that cure to a gelled or tacky state after an initial exposure to ultraviolet light, and are non-toxic in their cured form. In one embodiment, the UV layer is slightly flexible and is comprised of approximately 10-70% by weight of Aliphatic Urethane Acrylates. In another embodiment, the UV layer is comprised of approximately 15-50% by weight of Aliphatic Urethane Acrylates. And in yet another embodiment, the UV layer is comprised of approximately 20-40% by weight of Aliphatic Urethane Acrylates. The UV layer may also be clear translucent, translucently pigmented, or non-translucent.

In another embodiment, the UV layer has a composition range, by weight, of:

10-25% Polyurethane resin;
1-25% Epoxy resin;
1-20% Polyacrylate resin; and
1-10% Photoinitiators and stabilizers.

Additionally, numerous other materials are available commercially for use in the UV layer, and include polyurethane resins, epoxy resins, polyacrylate resins, and mixtures thereof. Additionally, a chemical blend of the UV layers may comprise one or more of the following compounds: acrylates, methacrylates, methyl acrylates, urethane or polyurethane(meth)acrylates, urethane methacrylates, ethyl methacrylate (EMA), polymethyl methacrylate (PMMA), hydroxyl ethyl acrylate (HEMA), triethylene glycol dimethacrylate, aliphatic urethane acrylates, aromatic urethane acrylates, lauryl acrylate, isooctyl acrylate, butyl acrylate, 2-ethylhexyl acrylate, hydroxypropyl acrylate, butyl methacrylate, isobutyl methacrylate, isobornyl methacrylate, isobornyl acrylate, 1,3-D glycol diacrylate, neopentyl glycol diacrylate, (2) propoxylatedneopentyl glycol diacrylate, polyethylene glycol dimethacrylate, triethylene glycol oxide dimethacrylate, tripropylene glycol diacrylate, trimethylolpropanetriacrylate, pentaerythritoltriacrylate, and (3) propoxylatedtrimethylol propane triacrylate.

Turning to the metal foil or film layer 40, 58, 78 in FIGS. 2-4, respectively, there are numerous commercially-available products that are suitable for use in the present invention. These products generally comprise a metallic film deposited on a plastic sheet (also referred to as a "metallized plastic sheet"). Such products are available in a number of metallic colors, including silver and gold, in multicolored forms, or in a holographic-finished form. Aluminum is the metal most commonly-available on plastic sheet, with polyethylene terephthalate (PET) being among the most commonly-used plastics. The metal films may have thicknesses in the range of 10-1000 nm, more typically 50-100 nm for aluminum. These thicknesses are sometimes expressed in the angstrom units (A), in which 1 nm equals 10 Å. At such thicknesses, the metallic film can readily be transferred intact onto an adhesive surface, such as that of UV adhesive layer by simple contact between the film and the adhesive. The resulting foil or film layer is typically porous (i.e., there are very small gaps between metallic particles), but it appears to be solid in the appliqué, and may be highly reflective. Because the metallic film is porous and so thin, it may deform (e.g., stretch) to some degree without adversely affecting the decoration of the appliqué. There are numerous cold-stamp foils suitable for use with the present invention that will be recognized by those having ordinary skill in the art and possession of the present disclosure.

In a method of fabricating a nail appliqué, according to an embodiment of the present invention, a laminated sheet of material is prepared having the layered structure desired for the nail appliqué. The sheet is built up in a layer-by-layer fashion on the releasable substrate 12, 32, 62, 82 by a continuous fabrication process. Such a continuous process is discussed in the aforesaid U.S. patent application Ser. No. 11/126,862 with regard to nail enamel appliqués, and suitable adaptations of this process for use in the present invention will be apparent to those having ordinary skill in the art and in possession of the present disclosure.

Using nail appliqué 10 in FIG. 1 as a non-limiting example, the adhesive layer 14 is deposited directly onto the substrate 12 as a liquid or by melting a solid adhesive onto the substrate 12. Suitable means for depositing an adhesive layer onto a surface during a continuous fabrication process are known in the art. The adhesive is allowed to gel or harden, while retaining its tackiness, before the next layer (i.e., base coat 16) is applied.

Turning to base coat 16, nail enamel is applied directly to the adhesive layer 14, so as to cover the adhesive layer 14, and form a smooth surface for subsequent application of the UV adhesive layer 18. Nail enamels containing organic solvents or water may be heated to evaporate a portion of the solvents or water, thus partially curing the base coat 16. The evaporation step may also be performed at room temperature, depending on the composition of the nail enamel used and the thickness of the base coat 16. The temperature and dwell time for this process are a matter of engineering choice, as they should be coordinated with the overall process rate and the desired quality of the final product. In embodiments of the present invention, a portion of the solvent or water is allowed to remain in the enamel (i.e., the enamel is "partially-cured"), so that the base coat 16 has a desired degree of stretch ability. If UV-curable nail enamel is used, a heating step may not be needed, since the typical UV-curable enamel typically would not contain solvents or water. Instead, the enamel would be exposed to UV radiation to initiate the curing process. The duration and intensity of the exposure would depend on the formulation of the nail enamel, and would be understood by those knowledgeable in the relevant chemical art, or could be selected according to instructions provided by the manufacturer of the nail enamel.

Turning to the UV adhesive layer 38 and foil layer 40 as illustrated in the embodiment of FIG. 2, the UV-curable mixture is applied to the surface of the base coat 36. In some embodiments of the present invention, the UV-curable mixture is not exposed to UV radiation until after the foil layer 40 is applied. In such an embodiment of the present invention, the metallic surface of a roll of metallized plastic sheet is put in contact with the UV-curable mixture using methods known in various arts (e.g., in continuous contact printing). The foil adheres to the UV-curable mixture in a porous layer and separates from the plastic sheet. This "cold stamping" process, which may be performed at room temperature, has advantages over the "hot stamping" process that is commonly used. Hot stamping requires that application of heat to the foil, which would heat the entire multilayered structure, causing the lower layers of the appliqué to dry out and, possibly, disrupting them. The hot stamping method also requires a die to transfer heat to the appliqué. Such dies often must be specially made. Neither a die nor the application of damaging degrees of heat are required for the cold stamping method used in embodiments of the present invention.

FIGS. 3 and 4 illustrate an embodiment in which the metallic foil layer is applied to the base color/design layer, and then the UV-cured layer is applied on top of the metallic layer.

After the foil layer 40 is applied, the UV-curable mixture is exposed to UV radiation through the porous metallic foil to initiate the curing process. As discussed with respect to the UV nail enamel of some embodiments of base coat 36, the duration and intensity of the exposure would depend on the formulation of the UV-curable mixture, and would be understood by those knowledgeable in the relevant chemical art, or could be selected according to instructions provided by the manufacturer of the adhesive.

Turning to the second nail enamel color/design layer 42, it is applied directly over the foil layer 40, so as to cover the foil layer 40 and the UV adhesive layer 38. The second color/design layer 42 can include a single layer or multiple layers of nail enamel. Nail enamels containing organic solvents or water may be heated to evaporate a portion of the solvents or water, thus partially curing the second (and first) color/design layers. The evaporation step may also be performed at room temperature, depending on the composition of the nail enamel used and the thickness of the layer 42. As with the base coat 36, the temperature and dwell time for this process are a matter of engineering choice, as they should be coordinated with the overall process rate and the desired quality of the final product. In embodiments of the present invention, a portion of the solvent or water is allowed to remain in the enamel (i.e., the enamel is "partially-cured"), so that the second layer 42 has a desired degree of stretch ability. If UV-curable nail enamel is used, a heating step may not be needed, since the typical UV-curable enamel typically would not contain solvents or water. Instead, the enamel would be exposed to UV radiation to initiate the curing process. The duration and intensity of the exposure would depend on the formulation of the nail enamel, and would be understood by those knowledgeable in the relevant chemical art, or could be selected according to instructions provided by the manufacturer of the nail enamel.

Laminated Sheets and Method of Use

Figure 5:
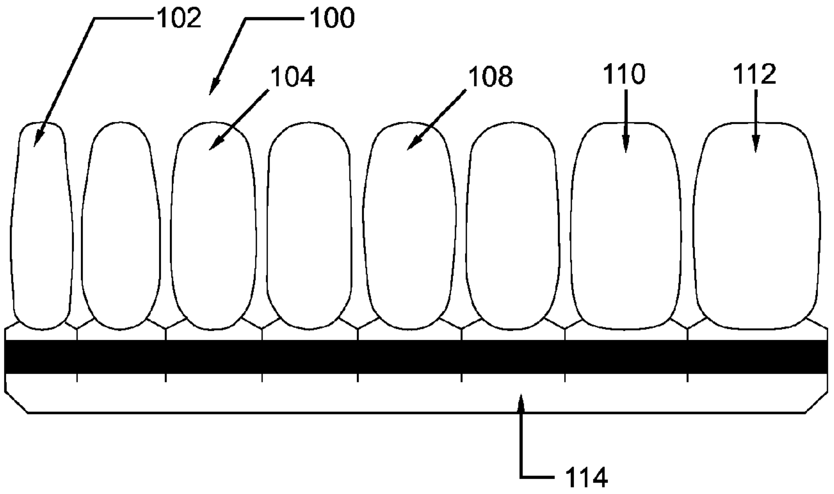

When the top coat 20, 42, 52, 72 in FIGS. 1-4, respectively, has been partially-cured, sets of nail appliqués on the substrate 12, 32, 62, 82 are cut from the laminated sheet. FIG. 5 is a schematic top plan view of an exemplary set 100 of nail appliqués made according to the foregoing method. Each set 100 may include appliqués of different sizes, such as appliqués 102, 104, 108, 110, 112 to accommodate nails of different sizes. In some embodiments, the appliqués 102, 104, 108, 110, 112 are integrated with a connector 114.

In some of the embodiments of the invention discussed above, the laminated sheet, and thus the nail appliqués, includes a small amount of solvent to keep the appliqués stretchable until they are used. Thus, the appliqué set 100 is sealed inside a package (not shown) that includes a vapor barrier to prevent the loss of solvent from the appliqués.

To use the nail appliqué, the user opens the package and removes the desired appliqué 102, 104, 108, 110, 112 from the connector 114. The user separates the appliqué from its substrate, and applies the adhesive layer (e.g. layer 14, 34, 64, 84 of FIGS. 1-4, respectively) to the nail. The user then stretches the appliqué to cover the nail, removes any excess appliqué overhanging the nail, and trims the appliqué to match the end of the nail (e.g., using a nail file). Body heat from the finger or toe completes the curing process, hardening the appliqué. Since the finished appliqué, as provided in the package, is thin (e.g., about 3.5-9.5 mil, or about 0.09-0.24 mm in overall thickness), the residual solvent can evaporate quickly (e.g., in less than an hour, depending on the user's body temperature and environmental conditions).

When the user desires to change the decoration of the nail appliqué, they merely remove the top coat(s) down to the UV layer comprising clear enamel and/or colored enamel and/or imprinted designs (e.g. FIG. 1, layer 20, FIG. 2, layers 40 and 42; FIG. 3, layer 72 and 74; FIG. 4 layer 92 and 94). The top coats down to the UV layer of the nail appliqué can be detached using methods routinely known in the art, such as: conventional nail polish remover applied to the top coats, and not the underlying coats; by rubbing the appliqué with a remover pad or cloth; and peeled off. For example in FIG. 2, nail appliqués that enable the user to peel off the top coats may further comprise an additional adhesive layer 40 (in lieu of metallic foil layer) directly above the UV layer.

It will be understood that the embodiments described herein are merely exemplary and that a person skilled in the art may make many variations and modifications without departing from the spirit and scope of the invention. All such variations and modifications are intended to be included within the scope of the invention, as embodied in the appended claims.

I claim:

1. A method of changing the decoration of a nail appliqué, by a user, from a first decoration to a second decoration, comprising the steps of:

a. providing a nail appliqué with a first decoration, comprising:
   i. a substrate layer;
   ii. a first adhesive layer onto the substrate layer;
   iii. a partially-cured base coat comprising a first colored enamel on top of the first adhesive layer;
   iv. a translucent or a translucently pigmented second adhesive UV layer on top of the base coat, wherein the second adhesive UV layer is curable by exposure to ultraviolet radiation and is able to protect the base coat from damage;
   v. a partially-cured top coat comprising a second colored enamel on top of the second adhesive UV layer, wherein said top coat is manually separable from said second adhesive UV layer;
   vi. wherein the nail appliqué is stretchable with the base coat, the second adhesive UV layer, and the top coat stretchable at substantially the same rates as each other;
b. detaching the first adhesive layer of the nail appliqué from the substrate layer;
c. applying the first adhesive layer onto a surface of a human nail wherein the adhesive layer secures the nail appliqué to the surface of the nail;
d. cutting the nail appliqué to more closely conform to the shape of the human nail, and allowing the nail appliqué to dry completely; and,
e. changing the nail appliqué decoration by the user manually removing the entire top coat comprising the second colored enamel by the user without damaging the nail appliqué to provide the appliqué with a second decoration comprising the translucent or translucently pigmented second adhesive UV layer covering the base coat comprising the first colored enamel, wherein the remaining applique layers remain fully intact.

2. The method of changing the decoration of a nail appliqué of claim 1, further comprising:

a. providing atop the second adhesive UV layer of the nail appliqué a metallic cold-stamped foil layer comprising a porous metal film with a plastic sheet removed;
b. passing ultraviolet radiation through the porous metal film to cure the second adhesive UV layer;
c. changing the nail appliqué decoration by the user manually removing the entire top coat without damaging the underlying layers, to display the appliqué with a second decoration comprising the metallic foil layer, and the translucent or translucently pigmented second adhesive UV layer covering the base coat comprising the first colored enamel, wherein the remaining appliqué layers are fully intact.

3. The method of changing the decoration of a nail appliqué of claim 1, further comprising providing a design imprinted on the top coat comprising the second colored enamel layer and/or on the base coat comprising the first colored enamel layer.

4. The method of changing the decoration of a nail appliqué of claim 1, further comprising:

a. providing atop the second adhesive UV layer a metallic cold-stamped foil layer of a metallized plastic sheet comprising a porous metal film with a plastic sheet removed;
b. passing ultraviolet radiation through to cure the second adhesive UV layer; and
c. changing the nail appliqué decoration by the user manually removing the entire top coat and the entire metallic cold-stamped foil layer without damaging the underlying layers to display the appliqué with a second decoration comprising the translucent or translucently pigmented second adhesive UV layer covering the base coat comprising the first colored enamel, wherein the remaining appliqué layers are fully intact.

5. The method of claim 1, wherein the entire top coat is peeled off to expose the underlying layer, and without damaging the second UV adhesive layer, or the base coat comprising the first colored enamel layer.

6. The method of claim 2, wherein the entire top coat is peeled off to expose the underlying metallic cold-stamped foil layer, and without damaging the metallic cold-stamped foil layer, the second adhesive UV layer, or the base coat comprising the first colored enamel layer.

7. The method of claim 4, wherein the top coat and the metallic cold-stamped foil layer are peeled off without damaging the second adhesive UV layer, or the base coat comprising the first colored enamel layer.

8. The method of claim 2, wherein the base coat, the second adhesive UV layer, the metallic cold-stamped foil layer, and the top coat are coextensive with each other in an uncured state, a partially-cured state, and a cured state.

* * * * *